(12) United States Patent
Gil et al.

(10) Patent No.: US 10,961,274 B2
(45) Date of Patent: Mar. 30, 2021

(54) SELF-ASSEMBLING PEPTIDES COMPRISING NON-IONIC POLAR AMINO ACIDS FOR ANTI-ADHESION

(71) Applicant: 3-D Matrix, Ltd., Tokyo (JP)

(72) Inventors: Eun Seok Gil, Lexington, MA (US); Marc Rioult, Cambridge, MA (US); Keiji Nagano, Tokyo (JP); Karl Patrick Gilbert, Brighton, MA (US); Toshiro Kiyofuji, Tokyo (JP); Yuya Hasegawa, Tokyo (JP)

(73) Assignee: 3-D Matrix, Ltd., Tokyo (JP)

( * ) Notice: Subject to any disclaimer, the term of this patent is extended or adjusted under 35 U.S.C. 154(b) by 137 days.

(21) Appl. No.: 16/062,801

(22) PCT Filed: Dec. 15, 2016

(86) PCT No.: PCT/US2016/066859
§ 371 (c)(1),
(2) Date: Jun. 15, 2018

(87) PCT Pub. No.: WO2017/106460
PCT Pub. Date: Jun. 22, 2017

(65) Prior Publication Data
US 2020/0190144 A1 Jun. 18, 2020

Related U.S. Application Data

(60) Provisional application No. 62/267,621, filed on Dec. 15, 2015.

(51) Int. Cl.
| | |
|---|---|
| *C07K 7/08* | (2006.01) |
| *A61K 38/08* | (2019.01) |
| *A61L 27/22* | (2006.01) |
| *A61L 27/52* | (2006.01) |

(52) U.S. Cl.
CPC .............. *C07K 7/08* (2013.01); *A61K 38/08* (2013.01); *A61L 27/227* (2013.01); *A61L 27/52* (2013.01); *A61L 2400/06* (2013.01)

(58) Field of Classification Search
CPC ......... C07K 7/08; A61L 27/227; A61L 27/52; A61L 2400/06; A61K 38/08; A61K 38/04; A61K 38/03; A61P 17/02
See application file for complete search history.

(56) References Cited

U.S. PATENT DOCUMENTS

| | | | |
|---|---|---|---|
| 10,682,441 B2 * | 6/2020 | Gil | A61L 27/227 |
| 2008/0032934 A1 * | 2/2008 | Ellis-Behnke | A61L 26/0061 514/9.4 |
| 2009/0130455 A1 | 5/2009 | Mirkin et al. | |
| 2011/0318380 A1 | 12/2011 | Brix et al. | |

FOREIGN PATENT DOCUMENTS

| | | |
|---|---|---|
| WO | 2012016357 | 2/2012 |
| WO | 2014167350 | 10/2014 |

OTHER PUBLICATIONS

Zhang et al (Seminars in Cancer Biology, 2005, 15, 413-420) (Year: 2005).*
Protopapa, E., Ringstad, L., Aggeli, A.; Nelson, A. (2010). Interaction of self-assembling beta-sheet peptides with phospholipid monolayers: The effect of serine, threonine, glutamine and asparagine amino acid side chains. Electrochimica Acta, 55 (9), 3368-3375.

* cited by examiner

*Primary Examiner* — Sudhakar Katakam
(74) *Attorney, Agent, or Firm* — IP Supra, PLLC; Constantine Linnik

(57) ABSTRACT

Self-assembling peptides comprising non-ionic polar amino acids for anti-adhesion are provided herein. Compositions, peptide solutions and macroscopic scaffolds of self-assembling peptides consisting essentially of non-ionic, polar amino acids are provided to prevent adhesion or to provide anti-adhesion properties. Particular peptides include those consisting essentially of, serine, threonine, tyrosine, cysteine, glutamine, asparagine, methionine, tryptophan, hydroxy-proline, and combinations thereof. Methods and kits are also provided.

13 Claims, 9 Drawing Sheets

SELF-ASSEMBLING PEPTIDES COMPRISING NON-IONIC POLAR AMINO ACIDS FOR ANTI-ADHESION

CROSS-REFERENCE TO RELATED APPLICATION

This application is a § 371 National Stage Application of PCT/US2016/066859, filed Dec. 15, 2016, which claims priority to U.S. Provisional Patent Application Ser. No. 62/267,621, filed Dec. 15, 2015, the entire contents of which are hereby incorporated herein by reference in their entirety for all purposes.

FIELD OF THE TECHNOLOGY

One or more aspects relate generally to materials and methods that may be used in medical and research applications. More particularly, one or more aspects relate to materials and methods that may be used to provide peptide hydrogel materials.

SUMMARY

In accordance with one or more aspects, a composition for preventing adhesion comprising a self-assembling peptide consisting essentially of non-ionic, polar amino acids is provided.

In accordance with one or more aspects, a peptide solution for preventing adhesion comprising a self-assembling peptide consisting essentially of non-ionic, polar amino acids is provided.

In accordance with one or more aspects, a method for preventing adhesion in a subject is provided. The method comprises introducing a delivery device to the subject, and positioning an end of the delivery device in a target area of the subject in which adhesion prevention is desired. The method comprises administering through the delivery device a solution comprising a self-assembling peptide consisting essentially of non-ionic, polar amino acids, in an effective amount and in an effective concentration to form a hydrogel scaffold under conditions at the target site to provide adhesion prevention. The method comprises removing the delivery device from the target site.

In accordance with one or more aspects, a kit for preventing adhesion in a subject is provided. The kit comprises a solution comprising a self-assembling peptide consisting essentially of non-ionic, polar amino acids, in an effective amount and in an effective concentration to form a hydrogel scaffold under physiological conditions to prevent adhesion at a target site. The method comprises instructions for administering the solution to the target site of the subject.

BRIEF DESCRIPTION OF THE DRAWINGS

The accompanying drawings are not intended to be drawn to scale. For purposes of clarity, not every component may be labeled. In the drawings.

DETAILED DESCRIPTION

Figure 1:
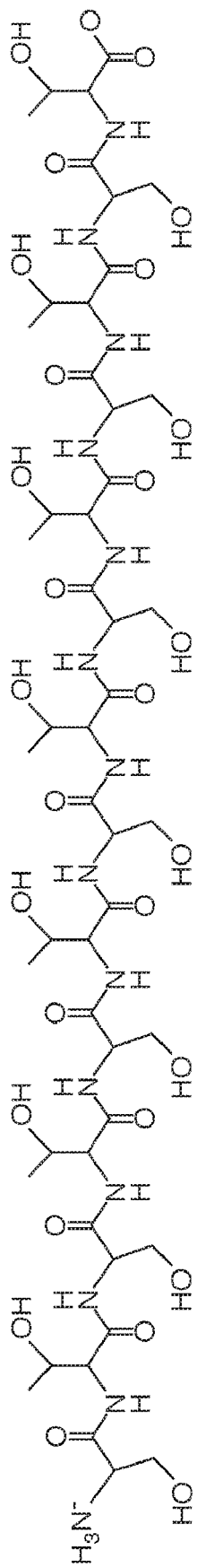
FIG. 1 is a chemical structure of ST14, in accordance with some embodiments.

The materials, systems and methods of the present disclosure may promote anti-adhesion.

Postoperative tissue adhesions occur widely in connection with various surgical procedures such as those relating to neurosurgery, thoracic surgery, digestive system surgery and orthopedic surgery. Adhesion is also a common problem in connection with various procedures performed in urology, obstetrics, gynecology, ophthalmology and other specialties. Adhesion generally relates to a physiological and biological repair reaction. Particularly following laparotomy, it is considered difficult to prevent such adhesion completely. The nature of adhesion is generally different from tissue to tissue. Thus, an anti-adhesion material which works in some situations does not necessarily perform well at another adhesion site.

Currently, sodium hyaluronate, carboxymethyl cellulose, oxidized regenerated cellulose, and expanded polytetrafluoroethylene (ePTFE) are widely used clinically as anti-adhesion materials. The efficacy of these materials is restrictive and there is dissatisfaction with them. In addition, each of these materials is provided in sheet form, so it is difficult to immobilize at the application site. They are also difficult to use during endoscopic surgeries. Such sheet materials also cannot be applied to bleeding sites.

In accordance with one or more embodiments, a self-assembling peptide hydrogel may be used as a material for tissue anti-adhesion. In some embodiments, the peptide solution or hydrogel may perform as a physical barrier until the site completes its repair reaction.

The materials, systems and methods of the present disclosure may promote anti-adhesion in epicardial ablation. Epicardial ablation of ventricular tachycardia is a relatively new technique for ablating abnormal heart rhythms that originate close to or on the surface of the epicardium. Epicardial ablation generally relates to ablation of cells on the outside of the heart muscle which may be used to identify regions of heart tissue responsible for rhythm problems. The conventional percutaneous approach to the pericardial space may be difficult in patients who have undergone cardiac surgery or epicardial ablation in the past due to adhesion. There are currently no approved materials that can be used clinically for epicardial ablation under a catheter approach.

In accordance with one or more embodiments, a self-assembling peptide hydrogel may be used as a material for tissue anti-adhesion under a catheter approach to epicardial ablation. In some embodiments, the peptide solution may perform as a physical barrier until the site completes its repair reaction.

The self-assembling peptides of the present disclosure may include application of the self-assembling peptides to a predetermined or desired target. The self-assembling peptide may be applied or introduced to a target site in the form of a composition, peptide solution, hydrogel, membrane or other form. A target site may be a predetermined area of a subject that requires a particular treatment.

In certain embodiments, a self-assembling peptide may be introduced to a target site of a subject. The subject may be a mammal, such as a human. The subject may be an animal. The introducing of the self-assembling peptide may be introduced by way of injection, but other conventional methods may be contemplated. The injection procedure may be a simple procedure, relative to surgery, and may be completed within a few hours.

In some embodiments, the target site may relate to a surgical site, such as an endoscopic surgical site. In some embodiments, the target site may relate to epicardial ablation, such as under a catheter approach. In other embodiments, the target site may be a bleeding site. The term "self-assembling peptide" may refer to a peptide that may exhibit a beta-sheet structure in aqueous solution in the presence of specific conditions to induce the beta-sheet structure. The specific conditions may include adjusting the pH of a self-assembling peptide solution. The adjustment may be an increase or a decrease in the pH of the self-assembling peptide solution. The adjustment of pH may be an adjustment, for example, an increase or decrease, in pH to a physiological pH. The specific conditions may also include adding a cation, such as a monovalent cation, to a self-assembling peptide solution. The specific conditions may include conditions related to the site of a surgery. The self-assembling peptides may be referred to as or be a part of a composition, peptide solution, hydrogel, or scaffold.

"Physiological conditions," such as a physiological pH or a physiological temperature, may occur in nature for a particular organism, cell system, or subject which may be in contrast to artificial laboratory conditions. The conditions may comprise one or more properties such as one or more particular properties or one or more ranges of properties. For example, the physiological conditions may include a temperature or range of temperatures, a pH or range of pH's, a pressure or range of pressures, and one or more concentrations of particular compounds, salts, and other components. For example, in some examples, the physiological conditions may include a temperature in a range of about 20 to about 40 degrees Celsius. In some examples, the atmospheric pressure may be about 1 atm. The pH may be in the range of a neutral pH. For example, the pH may be in a range of about 6 to about 8. In some instances, the physiological pH may be less than 6, for example, about 1-4, in the case of at least a portion of the gastric tract. The physiological conditions may include cations such as monovalent metal cations that may induce membrane or hydrogel formation. These may include sodium chloride (NaCl). The physiological conditions may also include a glucose concentration, sucrose concentration, or other sugar concentration, of between about 1 mM and about 20 mM. The physiological conditions may include the local conditions of the target site in some specific embodiments.

As used herein, the term "subject" is intended to include human and non-human animals, for example, vertebrates, large animals, and primates. In certain embodiments, the subject is a mammalian subject, and in particular embodiments, the subject is a human subject. Although applications with humans are clearly foreseen, veterinary applications, for example, with non-human animals, are also envisaged herein. The term "non-human animals" of the invention includes all vertebrates, for example, non-mammals (such as birds, for example, chickens; amphibians; reptiles) and mammals, such as non-human primates, domesticated, and agriculturally useful animals, for example, sheep, dog, cat, cow, pig, rat, among others.

The peptide solution may be an aqueous self-assembling peptide solution. The self-assembling peptide may be administered, applied, or injected in a solution that is substantially cell-free, or free of cells. In certain embodiments, the self-assembling peptide may be administered, applied, or injected in a solution that is cell-free or free of cells.

The self-assembling peptide may also be administered, applied, or injected in a solution that is substantially drug-free or free of drugs. In certain embodiments, the self-assembling peptide may be administered, applied, or injected in a solution that is drug-free or free of drugs. In certain other embodiments, the self-assembling peptide may be administered, applied, or injected in a solution that is substantially cell-free and substantially drug-free. In still further certain other embodiments, the self-assembling peptide may be administered, applied, or injected in a solution that is cell-free and drug free.

The peptide solution may comprise, consist of, or consist essentially of the self-assembling peptide. The self-assembling peptide may be in a modified or unmodified form. By modified, it is meant that the self-assembling peptide may have one or more domains that comprise one or more amino acids that, when provided in solution by itself, would not self-assemble. By unmodified, it is meant that the self-assembling peptide may not have any other domains other than those that provide for self-assembly of the peptide.

In accordance with one or more embodiments, self-assembling peptides are provided consisting essentially of non-ionic, polar amino acids. In yet other embodiments, self-assembling peptides are provided consisting of non-ionic polar amino acids. Compositions and peptide solutions may be provided that comprise, consist essentially of or consist of a self-assembling peptide.

The number or percentage of specific non-ionic, polar amino acids may be based on the peptide's ability to self-assemble. The compositions and peptide solutions may comprise or consist essentially of, or consist of self-assembling peptides consisting essentially of, or consist of, non-ionic, polar amino acids.

In some embodiments, the non-ionic polar amino acids of the self-assembling peptide may be selected from the group consisting of serine, threonine, tyrosine, cysteine, glutamine, asparagine, methionine, tryptophan, hydroxy-proline, and combinations thereof. The non-ionic polar amino acids of the self-assembling peptide may be selected from the group consisting of serine and threonine, and combinations thereof.

In certain embodiments, the self-assembling peptide, may have or comprise a number of amino acids, or have a peptide length that provides for self-assembling of the peptide. The self-assembling peptide may be longer than that length that may provide self-assembly of the peptide, although in certain instances it may not be desirable due to cost or aggregation of the peptides during or after self-assembly.

In certain embodiments, the self-assembling peptide may have, comprise, or consist essentially of between about 7 amino acids and about 200 amino acids. The self-assembling peptide may consist essentially of between about 7 amino acids and about 200 amino acids. The self-assembling peptide may consist essentially of about 7 amino acids. The self-assembling peptide may consist essentially of about 8 amino acids. The self-assembling peptide may consist essentially of about 10 amino acids. The self-assembling peptide may consist essentially of about 12 amino acids. The self-assembling peptide may consist essentially of about 14 amino acids. The self-assembling peptide may consist essentially of about 16 amino acids. The self-assembling peptide may consist essentially of about 18 amino acids. The self-assembling peptide may consist essentially of about 20 amino acids.

In some embodiments, the self-assembling peptide may comprise, consist essentially of, or consist of alternating non-ionic, polar amino acids. The self-assembling peptide, or the alternating non-ionic, polar amino acid portion of the peptide, may be of an appropriate or pre-determined length as described above.

By alternating, it is meant to include a series of three or more amino acids that alternate between a first non-ionic, polar amino acid and a second non-ionic, polar amino acid. In some embodiments, alternating is meant to include a series of three or more amino acids that alternate between a first non-ionic, polar amino acid, a second, non-ionic polar amino acid, and a third non-ionic, polar amino acid. In some embodiments, alternating is meant to include a series of four or more amino acids that alternate between a first non-ionic, polar amino acid, a second, non-ionic polar amino acid, a third non-ionic, polar amino acid, and a fourth non-ionic, polar amino acid. It need not include each and every amino acid in the peptide sequence alternating between a first non-ionic, polar amino acid and a second non-ionic, polar amino acid, or alternating between a first non-ionic, polar amino acid, a second non-ionic, polar amino acid, and a third non-ionic, polar amino acid, or alternating between a first non-ionic, polar amino acid, a second non-ionic, polar amino acid, a third non-ionic, polar amino acid, and a fourth non-ionic, polar amino acid. Self-assembling peptides having a peptide sequence that alternates between five or more non-ionic, polar amino acids are also contemplated.

In some embodiments, a self-assembling peptide may be provided that comprises, consists essentially of, or consists of consecutive non-ionic polar amino acids. The self-assembling peptide, or the consecutive non-ionic, polar amino acid portion of the peptide, may be of an appropriate or pre-determined length as described above.

By consecutive, it is meant to include a series of three or more amino acids that follow continuously, in unbroken succession. In certain embodiments, self-assembling peptides may be provided that comprise non-ionic, polar amino acids in a consecutive arrangement. For example, a self-assembling peptide may comprise consecutive non-ionic, polar amino acids. The non-ionic, polar amino acids that are consecutive may be the same non-ionic, polar amino acid.

In some embodiments, the self-assembling peptide may comprise, consist essentially of, or consist of alternating serine and threonine amino acids. In certain embodiments, a self-assembling peptide consisting essentially of 14 non-ionic, polar amino acids, alternating between serine and threonine is provided, in certain instances, referred to as ST14.

In some embodiments, a self-assembling peptide is provided consisting essentially of, or consisting of threonine amino acids. The self-assembling peptide may consist essentially of, or consist of 7 threonine amino acids. The self-assembling peptide may consist essentially of, or consist of at least 7 threonine amino acids. The self-assembling peptide may consist essentially of, or consist of 14 threonine amino acids, referred to as T14. In certain embodiments, the self-assembling peptide may consist essentially of, or consist of, at least 14 threonine amino acids.

ST14 and T14 are composed of amino acids with polar uncharged side chains, specifically of serine (Ser or S) and/or threonine (Thr or T). The side chain of serine is a primary alcohol, chemically equivalent to a substituted methanol. Also, the side chain of threonine contains a secondary alcohol and a methyl group. Considering the side groups, ST14 and T14 are similar to polyvinyl alcohol (PVC), where the side group is a primary alcohol like serine. PVC has been used in biomedical applications for its biocompatibility. Especially, PVC hydrogel has been utilized as an anti-adhesive membrane due to its inherent chemically anti-adhesive characteristics [2, 3]. For example, anti-adhesive hydrogel membrane can be applied for abdominal surgery that results adhesions with an incidence as high as 95%, which cause complications such as bowel obstruction, female infertility, and chronic pain. With a similarity of the inherent chemistry of ST14 and T14 to anti-adhesive PVC, ST14 and T14 hydrogels might provide superior benefits in many biomedical applications where other products might not be relevant or might have a limited efficacy.

ST14 is composed of serine and threonine, which are alternately sequenced to have fourteen amino acids in the structure, as shown below and in FIG. 1.

Figure 1

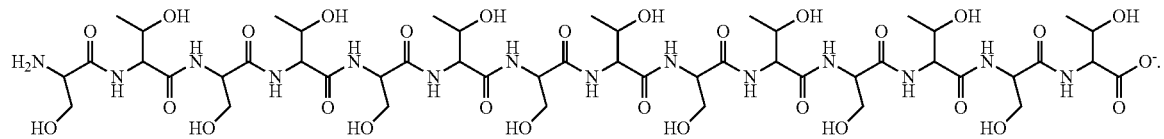

Chemical structure of ST14. ST14 has alternatively fourteen serines and threonines in its structure.

Figure 2:
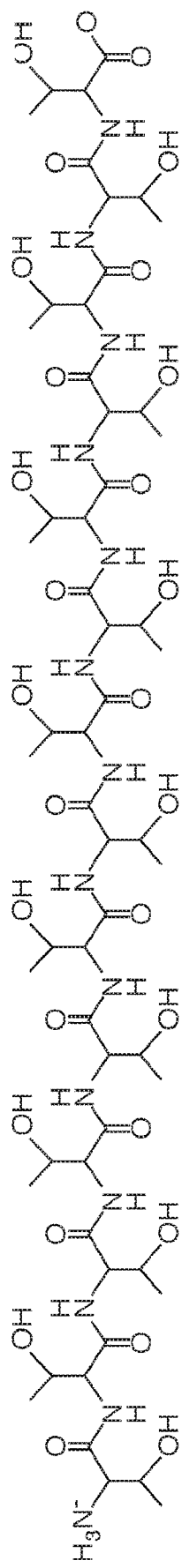
FIG. 2 is a chemical structure of T14, in accordance with some embodiments.

T14 is composed of only threonine, where fourteen threonines are sequenced in the structure, as shown below and in FIG. 2.

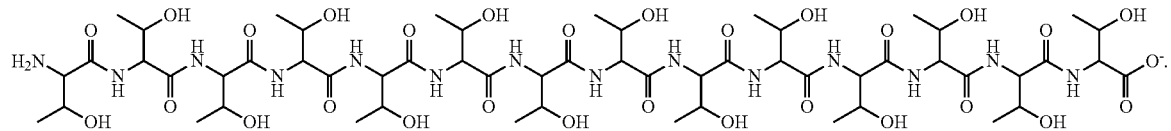

Figure 2

Chemical structure of T14. T14 has fourteen threonines in its structure.

The compositions, peptide solutions, and self-assembling peptides of the present disclosure may be capable of forming self-assembled nanofibers.

Peptide solutions and compositions may be provided comprising, consisting essentially of, or consisting of, self-assembling peptides consisting essentially of, or consisting of, non-ionic, polar amino acids.

The concentration of the self-assembling peptide in the peptide solution may be between about 0.1 weight per volume (w/v) percent to about 10 weight per volume (w/v) percent. In certain embodiments, the concentration of self-assembling peptide in the peptide solution is between about 0.5 weight per volume (w/v) percent and about 5 weight per volume (w/v) percent.

The pH of the peptide solution (of peptide in deionized water) may be between about 1.5 and about 3. In certain embodiments, the pH of the peptide solution may be between about 1.8 and about 2.7. In certain embodiments, the pH of the peptide solution may be between about 1.9 and 2.5. The pH of the peptide solution may vary depending upon various properties of the peptide, including the type of amino acids, length of peptide, and concentration of peptide in the solution.

In certain embodiments, the peptide solution may have a pH of between about 0.5 and about 8. The pH of the peptide solution may be adjusted to provide a peptide solution having a pH of between about 0.5 to about 8. In certain embodiments, the pH of the peptide solution may be adjusted to be between about 3 and about 8. The peptide solution may be changed or adjusted based on its desired use. For example a more neutral (a pH of between about 5 and 8) may be desirable for particular applications, for example, laboratory experiments. The same or different range of pH values may be desirable for other applications.

The peptide solution may have a storage modulus that increases by exposing the solution to conditions of higher pH. For example, by exposing the peptide solution to physiological conditions (for example, to a pH of between about 7 and about 8, or to a neutral pH) the storage modulus may increase between about 5 to about 10 times. The exposure may occur for a pre-determined time. For example, the exposure may occur for a time of about 30 seconds to about 60 minutes, or about 1 minute to about 30 minutes, or about 2 minutes to about 15 minutes. In some embodiments, the exposure may be for an indefinite period of time. In some embodiments the storage modulus of the peptide solution may increase about 7 times after exposure to physiological conditions. In certain embodiments, the concentration of peptide in the peptide solution is between about 0.1 weight per volume (w/v) percent and about 10 weight per volume (w/v) percent. In certain embodiments, the concentration of peptide in the peptide solution is between about 0.5 weight per volume (w/v) percent and about 5 weight per volume (w/v) percent. The concentration of the peptide solution may be about 1 (w/v) percent peptide.

In certain embodiments, the compositions and peptide solutions of the present disclosure may comprise cells. The cells may be, or may be derived from humans or other mammals. In certain embodiments, the cells may be mesenchymal stem cells. In some embodiments, the cells may be mouse mesenchymal stem cells. In some embodiments, the cells may be human mesenchymal stem cells. The concentration of cells in the solution may be about 5 million cells per milliliter. In some embodiments, the cell concentration may be less than 5 million cells per milliliter.

In certain embodiments, a method of treating a subject may be provided. The method may comprise introducing a delivery device to the subject, and positioning an end of the delivery device in a target area of the subject. The method may comprise administering through the delivery device a solution comprising, consisting essentially of, or consisting of a self-assembling peptide consisting essentially of, or consisting of non-ionic, polar amino acids as described throughout this disclosure. The non-ionic polar amino acids of the self-assembling peptide may be selected from the group consisting of serine, threonine, tyrosine, cysteine, glutamine, asparagine, methionine, tryptophan, hydroxyproline, and combinations thereof. The self-assembling peptide may comprise, consist essentially of, or consist of alternating serine and threonine, or may consist essentially of or consist of threonine. The administration is provided in an effective amount and in an effective concentration to form a hydrogel, for example, a hydrogel scaffold, under conditions at the target site. The method may further comprise removing the delivery device from the target site.

The term "administering" or "administered" is intended to include, but is not limited to, applying, introducing or injecting the self-assembling peptide, in one or more of various forms including, but not limited to, by itself, by way of solution, such as an aqueous solution, or by way of a composition, hydrogel, or scaffold, with or without additional components.

The method may comprise introducing a delivery device at or near a predetermined or desired target area of a subject. The method may comprise introducing a delivery device comprising at least one of a syringe, tube, pipette, catheter, catheter syringe, or other needle-based device to the predetermined or desired target area of a subject. The self-assembling peptide may be administered by way of a syringe, tube, pipette, catheter, catheter syringe, or other needle-based device to the predetermined or desired target area of a subject. The gauge of the syringe needle may be selected to provide an adequate flow of a composition, a solution, a hydrogel, or a liquid from the syringe to the target area. This may be based in some embodiments on at least one of the amount of self-assembling peptide in a composition, peptide solution, or a hydrogel being administered, the concentration of the peptide solution, in the composition, or the hydrogel, and the viscosity of the peptide solution, composition, or hydrogel. The delivery device may be a conventional device or designed to accomplish at least one of to reach a specific target area, achieve a specific dosing regime, deliver a specific target volume, amount, or concentration, and deliver accurately to a target area.

In certain embodiments, a method of preventing adhesion in a subject may be provided. The method may comprise introducing a delivery device to the subject in which adhesion is desired, and positioning an end of the delivery device in a target area of the subject. The method may comprise administering through the delivery device a solution comprising, consisting essentially of, or consisting a self-assembling peptide, as described herein, for example, consisting essentially of, or consisting of non-ionic, polar amino acids. The self-assembling peptide may comprise, consist essentially of alternating serine and threonine, or may consist essentially of or consist of threonine. The administration is provided in an effective amount and in an effective concentration to form a hydrogel scaffold under conditions at the target site to provide adhesion prevention. The method may further comprise removing the delivery device from the target site.

The use of a delivery device may provide a more selective administration of the peptide to provide for a more accurate delivery to the target area. Selective administration of the peptide may allow for enhanced and more targeted delivery of the peptide solution, composition, or hydrogel such that is successful and positioned in the desired location in an accurate manner. The selective administration may provide enhanced, targeted delivery that markedly improves the positioning and effectiveness of the treatment over use of a syringe or other delivery device. Delivery devices that may be used in the systems, methods, and kits of the disclosure may include a syringe, tube, needle, pipette, other needle-based device, or catheter.

Use of the delivery device may include use of accompanying devices, such as a guidewire used to guide the delivery device into position, or an endoscope that may allow proper placement of the delivery device and visualization of the target area, and/or the path to the target area. The endoscope may be a tube that may comprise at least one of a light and a camera or other visualization device to allow images of the subject's body to be viewed. The guidewire or endoscope may be introduced into the subject, for example, by way of an incision in the skin. The endoscope may be introduced to the target area prior to introducing the delivery device to the target area.

The use of the delivery device, such as a syringe, tube, needle, pipette, syringe catheter, other needle-based device, catheter, or endoscope may require determining the diameter or size of the opening in which there is a target area, such that at least a portion of the syringe, tube, needle, pipette, syringe catheter, other needle-type device, catheter, or endoscope may enter the opening to administer the peptide, peptide solution, composition, or hydrogel to the target area.

In certain embodiments, the hydrogel may be formed in vitro and administered to the desired location in vivo. In certain examples, this location may be the target area. In other examples, this location may be upstream, downstream of the area, or substantially near the area. It may be desired to allow a migration of the hydrogel to the area in which it is desired to. Alternatively, another procedure may position the hydrogel in the area in which it is desired treat a condition, for example, to provide anti-adhesion properties to a target area. The desired location or target area may be at least a portion of an area in which it is desired to treat a condition, for example, post-operative adhesion complications.

In certain aspects of the disclosure, the hydrogel may be formed in vivo. A solution comprising the self-assembling peptide, such as an aqueous solution, may be inserted to an in vivo location or area of a subject to prevent adhesion. In certain examples, the hydrogel may be formed in vivo at one location, and allowed to migrate to the area in which it is desired to provide anti-adhesion properties. The peptides of the present disclosure may be in the form of a powder, a solution, a gel, or the like. Since the self-assembling peptide gels in response to changes in solution pH and salt concentration, it can be distributed as a liquid that gels upon contact with a subject during application or administration.

In certain environments, the peptide solution may be a weak hydrogel and, as a result, it may be administered by way of a delivery device as described herein.

In accordance with one or more embodiments, a subject may be evaluated to determine a need to prevent adhesion. Once the evaluation has been completed, a peptide solution to administer to the subject may be prepared.

The hydrogel scaffold that is formed may be characterized by a storage modulus of greater than about 10 Pa. In certain embodiments, the hydrogel scaffold may be characterized by a storage modulus of greater than about 100 Pa. This may be determined, at least in part, by the concentration of the initial peptide solution administered. For example, in certain embodiments, without wishing to be bound by theory, the greater the concentration of the initial peptide solution, the higher the storage modulus of the hydrogel scaffold.

In certain embodiments, the method may comprise visualizing the target site. Visualizing the target area site may comprise visualizing the region or target area during at least one of identifying the target area, introducing the delivery device, positioning the end of the delivery device in the target area, administering the solution, removing the delivery device, and monitoring the target site thereafter. Visualizing the region or target area may provide for selective administration of the solution. Visualizing may occur at any time before, during, and after the administration of the solution. Visualization may occur, for example, at a predetermined period of time to assess the target site. Visualization may occur at a time period of at least one of about one week subsequent to administration, about four weeks subsequent to administration and about eight weeks subsequent to administration. The method may comprise visualizing the target site after a pre-determined period of time to assess adhesion prevention.

The concentration effective to form a hydrogel scaffold may comprise a concentration in a range of between about 0.5 weight per volume (w/v) percent and about 5 weight per volume (w/v) percent.

The concentration effective to prevent adhesion may comprise a concentration in a range of between about 0.5 weight per volume (w/v) percent and about 5 weight per volume (w/v) percent.

The pH of the peptide solution (of peptide in deionized water) to be administered may be between about 1.5 and about 3. In certain embodiments, the pH of the peptide solution (of peptide in deionized water) may be between about 1.8 and about 2.7. In certain embodiments, the pH of the peptide solution (of peptide in deionized water) may be between about 1.9 and 2.5. The pH of the peptide solution may vary depending upon various properties of the peptide, including the type of amino acids, length of peptide, and concentration of peptide in the solution.

In certain embodiments, the peptide solution to be administered may have a pH of between about 0.5 and about 8. The pH of the peptide solution may be adjusted to provide a peptide solution having a pH of between about 0.5 to about 8. In certain embodiments, the pH of the peptide solution may be adjusted prior to administration, for example, to be between about 3 and about 8.

The volume of the administered peptide solution may be selected so as to provide a desired treatment to the target area. For example, the volume of the administered peptide solution may be selected so as to provide a desired adhesion prevention to the target area. The volume of administered peptide solution may be between about 0.1 mL and about 10 mL. In some embodiments, the volume of the administered peptide solution may be between about 1 mL and about 5 mL.

The peptide solution may be substantially non-biologically active.

The method may further comprise mixing the peptide solution with a cell solution prior to administration. The cell solution may comprise mesenchymal stem cells. The cell solution may comprise human mesenchymal stem cells.

The methods of the present disclosure may be used after a surgical procedure, for example, a spine, cardio, or gastrointestinal procedure.

The hydrogel scaffold may have nanofibers having a diameter of between about 1 nanometer and about 20 nanometers. In certain embodiments, the hydrogel scaffold may comprise nanofibers having a diameter of less than about 5 nanometers.

The hydrogel scaffold may displace an interface between tissues to provide anti-adhesion properties. The hydrogel scaffold may disrupt connectivity between tissues, or between a tissue and a device. The methods and materials of the present disclosure may be used in a various clinical applications, for example, surgical procedures such as those relating to neurosurgery, thoracic surgery, digestive system surgery and orthopedic surgery. The methods and materials of the present disclosure may be used in various procedures performed in urology, obstetrics, gynecology, ophthalmology and other specialties.

The methods of the present disclosure may be used in a clinical application selected from the group consisting of obstetrics and gynecology.

A kit may be provided. The kit may comprise a solution comprising, consisting essentially of, or consisting of a self-assembling peptide consisting essentially of, or consisting of non-ionic, polar amino acids. The kit may comprise a solution comprising, consisting essentially of, or consisting of a self-assembling peptide comprising, consisting essentially of alternating serine and threonine, in an effective amount and in an effective concentration to form a hydrogel scaffold. The kit may comprise a solution comprising, consisting essentially of, or consisting of a self-assembling peptide consisting essentially of threonine in an effective amount and in an effective concentration to form a hydrogel scaffold. The solution may be provided in an effective amount and in an effective concentration to form a hydrogel scaffold under conditions, for example, physiological conditions, to prevent adhesion at a target site. The kit may also comprise instructions for administering the solution. The instructions may comprise instructions for administering the solution to the target site of the subject.

The kit may be provided for preventing adhesion in a subject. The effective amount and the effective concentration of the solution may be based in part on a dimension of the target site.

The concentration effective to form a hydrogel scaffold may comprise a concentration in a range of between about 0.5 weight per volume (w/v) percent and about 5 weight per volume (w/v) percent.

The concentration effective to prevent adhesion may comprise a concentration in a range of between about 0.5 weight per volume (w/v) percent and about 5 weight per volume (w/v) percent.

The pH of the peptide solution (of peptide in deionized water) to be administered may be between about 1.5 and about 3. In certain embodiments, the pH of the peptide solution (of peptide in deionized water) may be between about 1.8 and about 2.7. In certain embodiments, the pH of the peptide solution (of peptide in deionized water) may be between about 1.9 and 2.5. The pH of the peptide solution may vary depending upon various properties of the peptide, including the type of amino acids, length of peptide, and concentration of peptide in the solution.

In certain embodiments, the peptide solution to be administered may have a pH of between about 0.5 and about 8. The pH of the peptide solution may be adjusted to provide a peptide solution having a pH of between about 0.5 to about 8. In certain embodiments, the pH of the peptide solution may be adjusted, for example, prior to administration, to be between about 3 and about 8.

The peptide solution may be substantially non-biologically active.

The kit may further comprise a cell solution. The cell solution may comprise human cells. The cell solution may comprise mesenchymal stem cells. The cell solution may comprise human mesenchymal stem cells. The concentration of cells in the solution may be about 5 million cells per milliliter. In some embodiments, the cell concentration may be less than 5 million cells per milliliter.

The kits of the present disclosure may be used after a surgical procedure, for example, a spine, cardio, or gastrointestinal procedure.

The instructions for administering the solution may comprise methods for administering the peptide, peptide solution, or hydrogel provided herein, for example, by a route of administration described herein, at a dose, volume or concentration, or administration schedule.

The kit may also comprise informational material. The informational material may be descriptive, instructional, marketing, or other material that relates to the methods described herein. In one embodiment, the informational material may include information about production of the peptide, peptide solution, or hydrogel disclosed herein, physical properties of the peptide, composition, peptide solution or hydrogel, concentration, volume, size, dimensions, date of expiration, and batch or production site.

The kit may also optionally include a device or materials to allow for administration of the peptide or peptide solution to the desired area. For example, a syringe, pipette, tube, catheter, syringe catheter, or other needle-based device may be included in the kit. Additionally, or alternatively, the kit may include a guidewire, endoscope, or other accompanying equipment to provide selective administration of the peptide solution to the target area.

The kit may comprise in addition to or in the alternative, other components or ingredients, such as components that may aid in positioning of the peptide solution, hydrogel or scaffold. Instructions may be provided in the kit to combine a sufficient quantity or volume of the peptide solution with a sucrose solution that may or may not be provided with the kit. Instructions may be provided for diluting the peptide solution to administer an effective concentration of the solution to the target area. The instructions may describe diluting the peptide solution with a diluents or solvent. The diluents or solvent may be water. Instructions may further be provided for determining at least one of the effective concentration of the solution and the effective amount of the solution to the target area. This may be based on various parameters discussed herein, and may include the dimensions of the target area.

Other components or ingredients may be included in the kit, in the same or different compositions or containers than the peptide, peptide solutions, or hydrogel. The one or more components may include components that may provide for enhanced effectiveness of the self-assembling peptide or may provide another action, treatment, therapy, or otherwise interact with one or more components of the subject. For example, additional peptides comprising one or more biologically or physiologically active sequences or motifs may be included as one of the components along with the self-assembling peptide. Other components may include biologically active compounds such as a drug or other treatment that may provide some benefit to the subject. The peptide, peptide solution, or hydrogel may comprise small molecular drugs to treat the subject or to prevent hemolysis, inflammation, and infection, as disclosed herein. A sugar solution such as a sucrose solution may be provided with the kit. The sucrose solution may be a 20% sucrose solution. Other components which are disclosed herein may also be included in the kit.

In some embodiments, a component of the kit is stored in a sealed vial, for example, with a rubber or silicone closure (for example, a polybutadiene or polyisoprene closure). In some embodiments, a component of the kit is stored under inert conditions (for example, under nitrogen or another inert gas such as argon). In some embodiments, a component of the kit is stored under anhydrous conditions (for example, with a desiccant). In some embodiments, a component of the kit is stored in a light blocking container such as an amber vial.

As part of the kit or separate from a kit, syringes or pipettes may be pre-filled with a peptide, peptide solution, or hydrogel as disclosed herein. Methods to instruct a user to supply a self-assembling peptide solution to a syringe or pipette, with or without the use of other devices, and administering it to the target area through the syringe or pipette, with or without the use of other devices, is provided.

In accordance with one or more embodiments, a kit may include a syringe and a cannula to facilitate administration of the peptide solution. The kit may also include at least one wound dressing to facilitate healing and/or to hold the administered peptide solution in place. One or more materials to be mixed with the peptide solution prior to or during administration may be provided, such as an antibiotic or an anti-inflammatory agent.

In certain embodiments, the self-assembling peptides of the present disclosure, for example self-assembling peptides consisting essentially of, or consisting of non-ionic, polar amino acids are characterized by having stability (little or no degradation), or little or no change in molecular weight, after being autoclaved. The autoclaving process may be performed on the self-assembling peptide or self-assembling peptide solution, and may provide for a successful sterilization of the self-assembling peptide or self-assembling peptide solution with minimal or no degradation of the self-assembling peptide. Sterilization refers to a process that eliminates or kills at least a portion of microorganisms present, and may include elimination or reduction of at least a portion of all forms of life, including transmissible agents, such as microorganisms, fungi, bacteria, viruses, and spores, present in a fluid, compound, or material. Sterilization may include an elimination or reduction in microorganisms that would be suitable for its intended use. Sterilization may include an at least about 50%, 60%, 70%, 80%, 90%, 95%, 97%, 98%, 99%, 99.5%, 99.9% elimination or reduction of all forms of life, including transmissible agents, such as microorganisms, fungi, bacteria, viruses, and spores, present in a fluid, compound, or material. Sterilization may include a 100% elimination or reduction of all forms of life, including transmissible agents, such as microorganisms, fungi, bacteria, viruses, and spores present. The autoclaving process may be performed using any conventional autoclaving procedure, for example at 121° C. at saturated steam for a predetermined period of time. The time for autoclaving may be between about 1 minute and about 30 minutes. In certain embodiments, the predetermined time may be at least about 3 minutes. In certain embodiments, the predetermined time may be at least about 15 minutes. In certain other embodiments, the predetermined time may be at least about 25 minutes. The successful autoclaving of these peptides provides a consistent procedure for sterilizing the peptides and peptide solutions of any concentration, and avoids potential problems that may occur with filtering peptide solutions of higher concentrations. Particular peptides that have stability during the autoclaving process include those of the present disclosure, including ST14 and T14.

Methods may be provided for sterilizing self-assembling peptides of the present disclosure. The method may comprise providing a self-assembling peptide, or a self-assembling peptide solution, consisting essentially of, or consisting of non-ionic, polar amino acids. The peptide solution may comprise or consist essentially of a self-assembling peptide comprising at least one of a peptide consisting essentially of threonine, and a peptide consisting essentially of alternating serine and threonine. The method may comprise treating the peptide solution at a predetermined temperature and a predetermined pressure for a predetermined period of time to sterilize the peptide solution, the predetermined temperature and predetermined pressure selected to provide conditions of saturated steam.

The method may further comprise measuring the molar mass of the self-assembling peptide in the peptide solution prior to treating the peptide solution. The method may further comprise measuring the molar mass of the self-assembling peptide in the peptide solution subsequent to treating the peptide solution. The method may further comprise comparing the molar mass of the self-assembling peptide in the peptide solution prior to treating the peptide solution, with the molar mass of the self-assembling peptide in the peptide solution subsequent to treating the peptide solution. Treating the peptide solution may comprise treating the peptide solution in an autoclave.

As discussed, the temperature and pressure may be selected to provide conditions of saturated steam. For example, the temperature may be about 121° C. and the pressure may be about 15 psi. The temperature may be about 132° C. and the pressure may be about 30 psi.

The predetermined period of time may be between about 1 minute and about 30 minutes. In certain embodiments, the predetermined time may be at least about 3 minutes. In certain embodiments, the predetermined time may be at least about 15 minutes. In certain other embodiments, the predetermined time may be at least about 25 minutes.

Exemplary conditions may include those in Table 1.

TABLE 1

| Temperature | Pressure | Time |
| --- | --- | --- |
| 121° C. | 15 psi | 25 minutes |
| 121° C. | 15 psi | 15 minutes |
| 132° C. | 30 psi | 3 minutes |
| 132° C. | 30 psi | 8 minutes |
| 132° C. | 30 psi | 10 minutes |

In this regard, peptide solutions or peptides of this disclosure may be provided that have been sterilized by autoclaving.

Sterilization by gamma irradiation may also be performed on the peptide or peptide solution. Peptides or peptide solutions of this disclosure may be provided that have been sterilized by gamma irradiation.

In certain embodiments, the hydrogel of the self-assembling peptides disclosed herein (for example, peptide hydrogel scaffold) may be formed in vitro and administered to the desired location in vivo. In certain examples, this location may be the area in which it is desired to prevent adhesion. In other examples, this location may be upstream, downstream of the area, or substantially near the area. It may be desired to allow a migration of the hydrogel to the area in which it is desired to prevent adhesion. Alternatively, another procedure may position the hydrogel in the area in which it is desired. The desired location or target area may be at least a portion of an area associated with a surgical procedure, for example, an area in which adhesion prevention is desired.

In certain aspects of the disclosure, the hydrogel may be formed in vivo. A solution comprising the self-assembling peptide, such as an aqueous solution, may be inserted to an in vivo location or area of a subject to prevent or reduce adhesion at that location. In certain examples, the hydrogel may be formed in vivo at one location, and allowed to migrate to the area in which it is desired to prevent adhesion. Alternatively, another procedure may place the hydrogel in the area in which it is desired to prevent adhesion. The peptides of the present disclosure may be in the form of a powder, a solution, a gel, or the like. Since the self-assembling peptide gels in response to changes in solution pH and salt concentration, it can be distributed as a liquid that gels upon contact with a subject during application or administration.

In certain environments, the peptide solution may be a weak hydrogel and, as a result, it may be administered by way of a delivery device as described herein.

In accordance with one or more embodiments, self-assembling peptides may prevent adhesion, for example between two tissues of a subject, or between tissue of a subject and a medical device or instrument. In certain embodiments, this may be because the hydrogel, once in place, provides a scaffold to allow for a barrier or surface to prevent adhesion between two tissues or tissue and medical device or instrument.

In accordance with one or more embodiments, a macroscopic scaffold is provided. The macroscopic scaffold may comprise, consist essentially of, or consist of a plurality of self-assembling peptides, each of which comprises, consists essentially of, or consists of between about 7 and about 200 non-ionic, polar amino acids. In some embodiments, the non-ionic polar amino acids of the self-assembling peptide may be selected from the group consisting of serine, threonine, tyrosine, cysteine, glutamine, asparagine, methionine, tryptophan, hydroxy-proline, and combinations thereof. The non-ionic polar amino acids of the self-assembling peptide may be selected from the group consisting of serine and threonine, and combinations thereof. The non-ionic, polar amino acids of the self-assembling peptide may be threonine. The macroscopic scaffold may comprise, consist essentially of, or consist of any of the peptides discussed in this disclosure. The macroscopic scaffold may be provided to prevent adhesion. In certain embodiments, the macroscopic scaffold or the peptides may be referred to as "anti-adhesion macroscopic scaffolds" or "anti-adhesion peptides."

In accordance with one or more embodiments, a subject may be evaluated to determine a need for prevention of adhesion. Once the evaluation has been completed, a peptide solution to administer to the subject may be prepared.

In some embodiments, a biologically active agent may be used with the materials and methods of the present disclosure. A biologically active agent may comprise a compound, including a peptide, DNA sequence, chemical compound, or inorganic or organic compound that may impart some activity, regulation, modulation, or adjustment of a condition or other activity in a subject or in a laboratory setting. The biologically active agent may interact with another component to provide such activity. The biologically active agent may be referred to as a drug in accordance with some embodiments herein. In certain embodiments, one or more biologically active agents may be gradually released to the outside of the peptide system. For example, the one or more biologically active agents may be gradually released from the hydrogel. Both in vitro and in vivo testing has demonstrated this gradual release of a biologically active agent. The biologically active agent may be added to the peptide solution prior to administering to a subject, or may be administered separately from the solution to the subject.

This disclosure relates to aqueous solutions, hydrogels, scaffolds, and membranes comprising self-assembling peptides, sometimes referred to as self-assembling oligopeptides. The self-assembling peptides may exhibit a beta-sheet structure in aqueous solution in the presence of physiological pH and/or a cation, such as a monovalent cation, or other conditions applicable to a subject.

The self-assembling peptides may be generally stable in aqueous solutions and self-assemble into large, macroscopic structures, scaffolds, or matrices when exposed to physiological conditions, neutral pH, or physiological levels of salt. Once the hydrogel is formed it may not decompose, or may decompose or biodegrade after a period of time. The rate of decomposition may be based at least in part on at least one of the amino acid sequence and conditions of its surroundings.

By "macroscopic" it is meant as having dimensions large enough to be visible under magnification of 10-fold or less. In preferred embodiments, a macroscopic structure is visible to the naked eye. A macroscopic structure may be transparent and may be two-dimensional, or three-dimensional. Typically each dimension is at least 10 μm, in size. In certain embodiments, at least two dimensions are at least 100 μm, or at least 1000 μm in size. Frequently at least two dimensions are at least 1-10 mm in size, 10-100 mm in size, or more.

In certain embodiments, the size of the filaments may be about 10 nanometers (nm) to about 20 nm. The interfilament distance may be about 50 nm to about 80 nm. In some embodiments, the size of the filaments, for example, the diameter of the filaments, may be about 5 nm. In certain embodiments, the size of the filaments, for example, the diameter of the filaments, may be less than about 5 nm.

The peptides may also be complementary and structurally compatible. Complementary refers to the ability of the peptides to interact through ionized pairs and/or hydrogen bonds which form between their hydrophilic side-chains, and structurally compatible refers to the ability of complementary peptides to maintain a constant distance between their peptide backbones. Peptides having these properties participate in intermolecular interactions which result in the formation and stabilization of beta-sheets at the secondary structure level and interwoven filaments at the tertiary structure level.

Both homogeneous and heterogeneous mixtures of peptides characterized by the above-mentioned properties may form stable macroscopic membranes, filaments, and hydrogels. Peptides which are self-complementary and self-compatible may form membranes, filaments, and hydrogels in a homogeneous mixture. Heterogeneous peptides, including those which cannot form membranes, filaments, and hydrogels in homogeneous solutions, which are complementary and/or structurally compatible with each other may also self-assemble into macroscopic membranes, filaments, and hydrogels.

The membranes, filaments, and hydrogels may be non-cytotoxic. The hydrogels of the present disclosure may be digested and metabolized in a subject. The hydrogels may be biodegraded in 30 days or less. They have a simple composition, are permeable, and are easy and relatively inexpensive to produce in large quantities. The membranes and filaments, hydrogels or scaffolds may also be produced and stored in a sterile condition. The optimal lengths for membrane formation may vary with at least one of the amino acid composition, solution conditions, and conditions at the target site.

Methods of facilitating embodiments of the present disclosure may comprise providing instructions for administering through a delivery device a solution comprising a self-assembling peptide disclosed herein. The method of facilitating may be performed to prevent adhesion, and may be performed under physiological conditions.

Each of the peptide sequences disclosed herein may provide for peptides comprising, consisting essentially of, and consisting of the amino acid sequences recited.

The present disclosure provides materials, methods, and kits for solutions, hydrogels, and scaffolds comprising, consisting essentially of, or consisting of the peptides recited herein.

The self-assembly of the peptides may be attributable to hydrogen bonding and hydrophobic bonding between the peptide molecules by the amino acids composing the peptides.

The self-assembling peptides of the present disclosure may have a nanofiber diameter in a range of about 10 nm to about 20 nm and an average pore size is in a range of about 5 nm to about 200 nm. In some embodiments, the self-assembling peptides of the present disclosure may have a nanofiber diameter of about 5 nm or less than about 5 nm. In certain embodiments, the nanofiber diameter, the pore size, and the nanofiber density may be controlled by at least one of the concentration of peptide solution used and the amount of peptide solution used, such as the volume of peptide solution. As such, at least one of a specific concentration of peptide in solution and a specific amount of peptide solution to provide at least one of a desired nanofiber diameter, pore size, and density to adequately provide for adhesion prevention.

As used herein, an amount of a peptide, peptide solution or hydrogel effective to prevent adhesion, an "effective amount" or a "therapeutically effective amount," refers to an amount of the peptide, peptide solution or hydrogel, which is effective, upon single or multiple administration (application or injection) to a subject, in preventing adhesion beyond that expected in the absence of such treatment. This may include a particular concentration or range of concentrations of peptide in the peptide solution or hydrogel and additionally, or in the alternative, a particular volume or range of volumes of the peptide solution or hydrogel. The method of facilitating may comprise providing instructions to prepare at least one of the effective amount and the effective concentration.

The dosage, for example, volume or concentration, administered (for example, applied or injected) may vary depending upon the form of the peptide (for example, in a peptide solution, hydrogel, or in a dried form, such as a lyophilized form) and the route of administration utilized. The exact formulation, route of administration, volume, and concentration can be chosen in view of the subject's condition and in view of the particular target area or location that the peptide solution, hydrogel, or other form of peptide will be administered. Lower or higher doses than those recited herein may be used or required. Specific dosage and treatment regimens for any particular subject may depend upon a variety of factors, which may include the specific peptide or peptides employed, the dimension of the area that is being treated, the desired thickness of the resulting hydrogel that may be positioned in the desired target area, and the length of time of treatment. Other factors that may affect the specific dosage and treatment regimens include age, body weight, general health status, sex, time of administration, rate of degradation, the severity and course of the disease, condition or symptoms, and the judgment of the treating physician. In certain embodiments, the peptide solution may be administered in a single dose. In other embodiments, the peptide solution may be administered in more than one dose, or multiple doses. The peptide solution may be administered in at least two doses.

An effective amount and an effective concentration of the peptide solution may be selected to at least partially prevent adhesion. In some embodiments, at least one of the effective amount and the effective concentration may be based in part on a dimension or diameter of the target area and/or the amount of adhesion prevention desired or required.

The effective amount may be, as described herein, an amount that may provide for an at least partial adhesion prevention in a subject. Various properties of the target site may contribute to the selection or determination of the effective amount including at least one of the dimension or diameter of the target area, the flow rate of one or more fluids at or near the target area, the pH at or near the target area, and the concentration of various salts at or near the target area. Additional properties that may determine the effective amount include various properties listed above, at various locations along a pathway in which the peptide solution is delivered.

The effective amount may include volumes of from about 0.1 milliliters (mL) to about 100 mL of a peptide solution. The effective amount may include volumes of from about 0.1 mL to about 10 mL of a peptide solution. The effective amount may include volumes of from about 1 mL to about 5 mL of a peptide solution. In certain embodiments, the effective amount may be about 0.5 mL. In other embodiments, the effective amount may be about 1.0 mL. In yet other embodiments, the effective amount may be about 1.5 mL. In still yet other embodiments, the effective amount may be about 2.0 mL. In some other embodiments, the effective amount may be about 3.0 mL. In certain embodiments, the effective amount may be approximately 0.1 mL to about 5 mL per 1 cm² of target area. In certain embodiments, the effective amount may be approximately 1 mL per 1 cm² of target area. This effective amount may be related to a concentration, such as a 2.5 weight per volume percent of a peptide solution of the present disclosure.

The effective concentration may be, as described herein, an amount that may provide for a desired level of adhesion prevention, or "anti-adhesion." Various properties of the target site may contribute to the selection or determination of the effective concentration including at least one of a dimension or diameter of the target area.

The effective concentration may include peptide concentrations in the solution in a range of about 0.1 w/v percent to about 10 w/v percent. The effective concentration may include peptide concentrations in the solution in a range of about 0.5 w/v percent to about 5 w/v percent. In certain embodiments, the effective concentration may be about 3 w/v percent. In other embodiments, the effective concentration may be about 2.5 w/v percent.

In certain embodiments, a peptide solution having a higher concentration of peptide may provide for a more effective hydrogel that has the ability to stay in place and provide effective adhesion prevention. For purposes of delivering the peptide solution, higher concentrations of peptide solutions may become too viscous to allow for effective and selective administration of the solution. It is possible that if a high enough concentration is not selected, the hydrogel may not be effective at preventing adhesion at the target area for the desired period of time. The effective concentration may be selected to provide for a solution that may be administered by injection or other means using a particular diameter needle or other delivery device.

Methods of the disclosure contemplate single as well as multiple administrations of a therapeutically effective amount of the peptides, compositions, peptide solutions, membranes, filaments, and hydrogels as described herein. Peptides as described herein may be administered at regular intervals, depending on the nature, severity and extent of the subject's condition. In some embodiments, a peptide, composition, peptide solution, membrane, filament, or hydrogel may be administered in a single administration. In some embodiments, a peptide, composition, peptide solution, or hydrogel described herein is administered in multiple administrations. In some embodiments, a therapeutically effective amount of a peptide, composition, peptide solution, membrane, filament, or hydrogel may be administered periodically at regular intervals. The regular intervals selected may be based on any one or more of the initial peptide concentration of the solution administered, the amount administered, and the degradation rate of the hydrogel formed. For example, after an initial administration, a follow-on administration may occur after, for example, one week, two weeks, four weeks, six weeks, or eight weeks. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject. The predetermined intervals may be the same for each follow-on administration, or they may be different. This may be dependent on whether the hydrogel formed from the previous administration is partially or totally disrupted or degraded. The follow-on administration may comprise administration of a solution having the same concentration of peptide and volume as the initial administration, or may comprise administration of a solution of lesser or great concentration of peptide and volume. The selection of the appropriate follow-on administration of peptide solution may be based on imaging the target area and the area surrounding the target area and ascertaining the needs based on the condition of the subject.

The self-assembling peptides of the present disclosure, such as ST14 and T14, may be peptide sequences that lack a distinct physiologically or biologically active motif or sequence, and therefore may not impair intrinsic cell function. Physiologically active motifs may control numerous intracellular phenomena such as transcription, and the presence of physiologically active motifs may lead to phosphorylation of intracytoplasmic or cell surface proteins by enzymes that recognize the motifs. When a physiologically active motif is present, transcription of proteins with various functions may be activated or suppressed. The self-assembling peptides of the present disclosure may lack such physiologically active motifs and therefore do not carry this risk. A sugar may be added to the self-assembling peptide solution to improve the osmotic pressure of the solution from hypotonicity to isotonicity, thereby allowing the biological safety to be increased. In certain examples, the sugar may be sucrose or glucose.

In accordance of one or more embodiments, a tonicity of the peptide solution may be hypotonic, isotonic, or hypertonic. In some specific non-limiting embodiments, the tonicity of the peptide solution may be isotonic. The tonicity of the peptide solution may be adjusted in various approaches. In some embodiments, the tonicity of the peptide solution may impact or adjust the tonicity associated with a site of administration of the peptide solution, such as but not limited to, an administration site associated with a subject such as a human body. For example, in some embodiments tonicity may be adjusted with a tonicity agent. The tonicity agent may be selected from the group consisting of but not limited to: dextrose, glycerin, mannitol, potassium chloride, and sodium chloride. In other embodiments, the tonicity of the peptide solution may be adjusted with at least one salt. The at least one salt may be selected from the group consisting of but not limited to: sodium chloride, potassium chloride, magnesium chloride, calcium chloride, and calcium sulfate. The at least one salt may include one or more salt forming cations and one or more salt forming anions. The one or more salt forming cations may be selected from the group consisting of but not limited to: ammonium, calcium, iron, magnesium, potassium, pyridinium, quaternary ammonium, and sodium. The one or more salt forming anions may be selected from the group consisting of but not limited to: acetate, carbonate, chloride, citrate, cyanide, fluoride, nitrate, nitrite, and phosphate.

The optimal lengths for membrane formation may vary with the amino acid composition. A stabilization factor contemplated by the peptides of the present disclosure is that complementary peptides maintain a constant distance between the peptide backbones.

The peptides can be chemically synthesized or they can be purified from natural and recombinant sources. Using chemically synthesized peptides may allow the peptide solutions to be deficient in unidentified components such as unidentified components derived from the extracellular matrix of another animal. This property therefore may eliminate concerns of infection, including risk of viral infection compared to conventional tissue-derived biomaterials. This may eliminate concerns of infection including infections such as bovine spongiform encephalopathy (BSE), making the peptide highly safe for medical use.

The initial concentration of the peptide may be a factor in the size and thickness of the membrane, hydrogel, or scaffold formed. In general, the higher the peptide concentration, the higher the extent of membrane or hydrogel formation. Hydrogels, or scaffolds formed at higher initial peptide concentrations (about 10 mg/ml) (about 1.0 w/v percent) may be thicker and thus, likely to be stronger.

Formation of the membranes, hydrogels, or scaffolds may occur based on the exposure of the peptide solution to select conditions. Formation of the membranes, hydrogels, or scaffolds may occur in a range on the order of seconds to on the order of minutes. For example, the formation may be instantaneous upon administration. In some embodiments, the formation upon administration may occur in less than 1 second. The formation upon administration may occur in less than 5 seconds, less than 30 seconds, less than 1 minute, less than 5 minutes, less than 15 minutes, or less than 30 minutes. The formation of the hydrogel may occur within about one to two minutes of administration. In other examples, the formation of the hydrogel may occur within about three to four minutes of administration. In certain embodiments, the formation may be reversible, and in other embodiments, the formation may be irreversible. In certain embodiments the time it takes to form the hydrogel may be based at least in part on one or more of the concentration of the peptide solution, the volume of peptide solution applied, and the conditions at the area of application or injection (for example, the concentration of monovalent metal cations at the area of application, the pH of the area, and the presence of one or more fluids at or near the area). The process may be unaffected by pH of less than or equal to 12, and by temperature. The membranes or hydrogels may form at temperatures in the range of about 1 to 99 degrees Celsius.

The hydrogels may remain in position at the target area for a period of time sufficient to provide a desired effect using the methods and kits of the present disclosure. The desired effect may be to prevent adhesion between two tissues of a subject, or a tissue area and a medical device or medical instrument.

The period of time that the membranes or hydrogels may remain at the desired area may be for one or more days, up to one or more weeks, and up to several months. In other examples, it may remain at the desired area for up to 30 days, or more. It may remain at the desired area indefinitely. In other examples, it may remain at the desired area for a longer period of time, until it is naturally degraded or intentionally removed. If the hydrogel naturally degrades over a period of time, subsequent application or injection of the hydrogel to the same or different location may be performed.

In certain embodiments, the self-assembling peptide may be prepared with one or more components that may provide for enhanced effectiveness of the self-assembling peptide or may provide another action, treatment, therapy, or otherwise interact with one or more components of the subject. For example, additional peptides comprising one or more biologically or physiologically active amino acid sequences or motifs may be included as one of the components along with the self-assembling peptide. Other components may include biologically active compounds such as a drug or other treatment that may provide some benefit to the subject. For example, an antibiotic may be administered with the self-assembling peptide, or may be administered separately.

The peptide, peptide solution, or hydrogel may comprise small molecular drugs to treat the subject or to prevent hemolysis, inflammation, and infection. The small molecular drugs may be selected from the group consisting of glucose, saccharose, purified saccharose, lactose, maltose, trehalose, destran, iodine, lysozyme chloride, dimethylisoprpylazulene, tretinoin tocoferil, povidone iodine, alprostadil alfadex, anise alcohol, isoamyl salicylate, $\alpha,\alpha$-dimethylphenylethyl alcohol, bacdanol, helional, sulfazin silver, bucladesine sodium, alprostadil alfadex, gentamycin sulfate, tetracycline hydrochloride, sodium fusidate, mupirocin calcium hydrate and isoamyl benzoate. Other small molecular drugs may be contemplated. Protein-based drugs may be included as a component to be administered, and may include erythropoietin, tissue type plasminogen activator, synthetic hemoglobin and insulin.

A component may be included to protect the peptide solution against rapid or immediate formation into a hydrogel. This may include an encapsulated delivery system that may degrade over time to allow a controlled time release of the peptide solution into the target area to form the hydrogel over a desired, predetermined period of time. Biodegradable, biocompatible polymers may be used, such as ethylene vinyl acetate, polyanhydrides, polyglycolic acid, collagen, polyorthoesters, and polylactic acid.

Any of the components described herein may be included in the peptide solution or may be administered separate from the peptide solution. Additionally, any of the methods and methods of facilitating provided herein may be performed by one or more parties.

In some embodiments of the disclosure, the self-assembling peptides may be used as a coating on a device or an instrument. The self-assembling peptides may also be incorporated or secured to a support, such as gauze or a bandage, or a lining, that may provide a therapeutic effect to a subject, or that may be applied within a target area. The self-assembling peptides may also be soaked into a sponge for use.

In accordance with one or more embodiments, macroscopic structures can be useful for culturing cells and cell monolayers. Cells prefer to adhere to non-uniform, charged surfaces. The charged residues and conformation of the proteinaceous membranes promote cell adhesion and migration. The addition of growth factors, such as fibroblast growth factor, to the peptide macroscopic structure can further improve attachment, cell growth and neurite outgrowth. The porous macrostructure can also be useful for encapsulating cells. The pore size of the membrane can be large enough to allow the diffusion of cell products and nutrients. The cells are, generally, much larger than the pores and are, thus, contained.

In accordance with one or more embodiments, a macroscopic scaffold comprises a plurality of self-assembling peptides, wherein the self-assembling peptides self-assemble into a β-sheet macroscopic scaffold and wherein said macroscopic scaffold encapsulates living cells and wherein said cells are present in said macroscopic scaffold in a three-dimensional arrangement. One or more embodiments also encompass methods of regenerating a tissue comprising administering to a mammal a macroscopic scaffold comprising the disclosed self-assembling peptides at a target site.

The function and advantage of these and other embodiments of the compositions, peptides, peptide solutions, methods and kits disclosed herein will be more fully understood from the examples below. The following examples are intended to illustrate the benefits of the disclosed peptides, peptides, solutions, methods and kits, but do not exemplify the full scope thereof.

EXAMPLES

Example 1: Morphological Studies

Atomic Force Microscopy (AFM) images of ST14 and T14 peptides were investigated to visualize their nano structures. Samples were prepared by placing an aliquot of approximately 50 microliters (μl) of the peptide (100 micromolar (μM)) solution on the surface (9 millimeters (mm) in diameter) of a mica surface. Each sample was left on the mica for about 30 seconds (s) and then rinsed with aliquots of 100 μl of Milli-Q (ultrapure) water to remove unattached peptides. The sample on the mica surface was then air-dried for AFM observation. AFM was performed with Asylum-1 MFP-3D AFM System (Asylum Research, Santa Barbara, Calif.) using a tapping mode. The images utilized an Olympus Si tip (AC240FS). The cantilever's free resonance frequency was 70 kHz. Height images were recorded with 256×256 pixels resolution.

Figure 3:
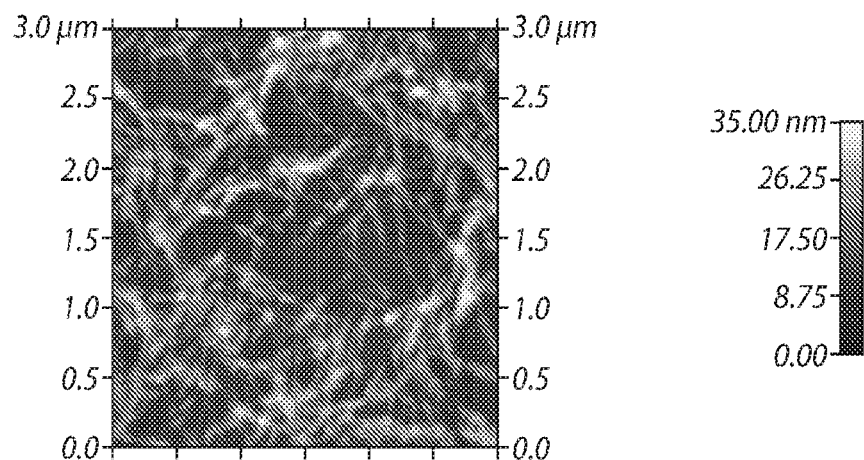
FIG. 3 is an image of peptide ST14, in accordance with some embodiments.
Figure 4:
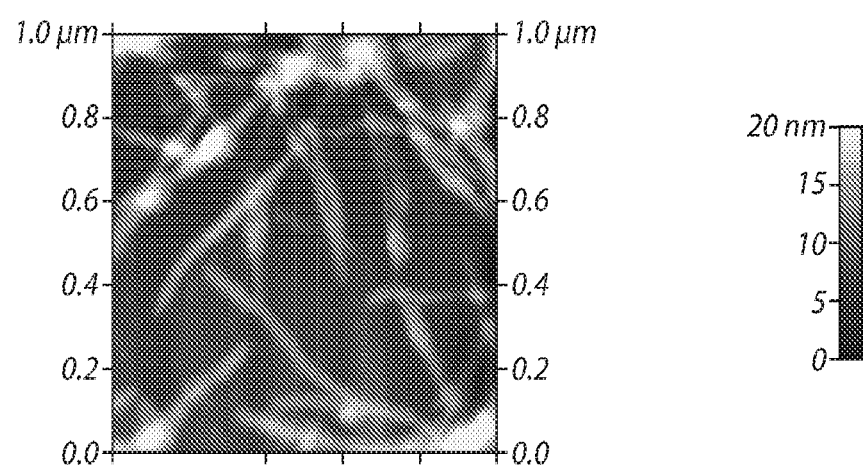
FIG. 4 is an image of peptide ST14, in accordance with some embodiments.
Figure 5:
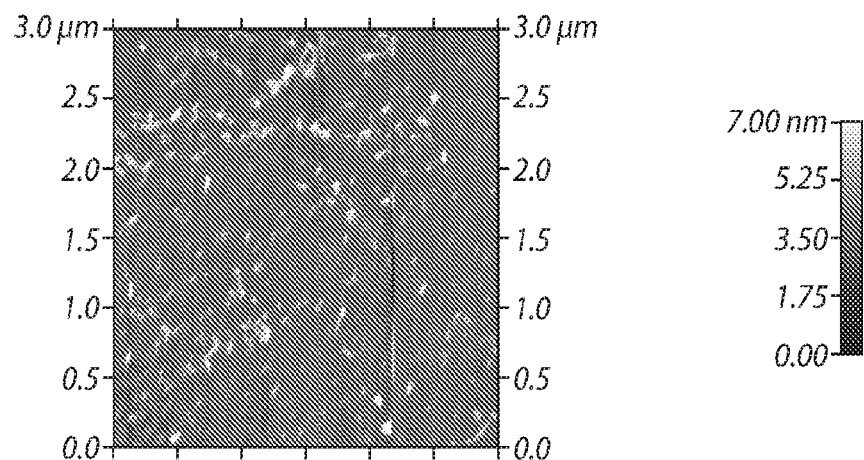
FIG. 5 is an image of peptide T14, in accordance with some embodiments.
Figure 6:
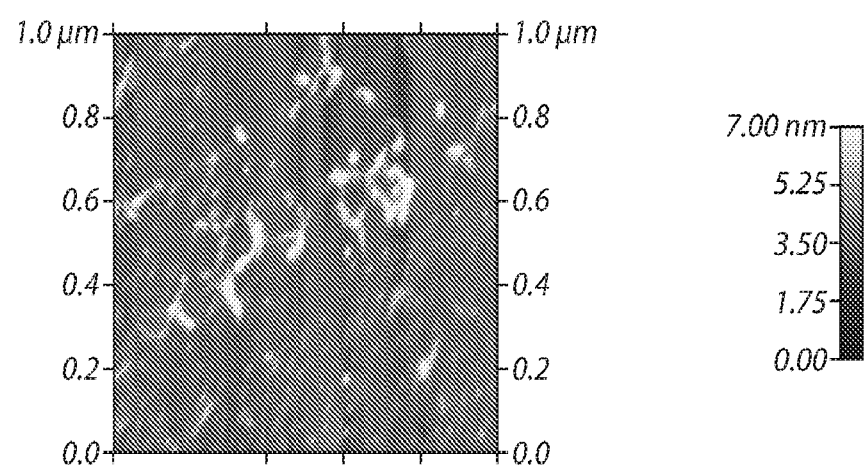
FIG. 6 is an image of peptide T14, in accordance with some embodiments.

As shown in FIGS. 3 and 4, AFM morphological studies demonstrated that ST14 forms self-assembled nanofibers. Aggregates have been detected in T14, as shown in FIGS. 5 and 6.

Example 2: Stability and Sterilization Studies

Sterilization is a very important step in the manufacturing process for all biomaterials, including the self-assembling peptide solutions. Autoclave treatment of the peptides appears to be the best sterilization method for highly viscous peptide solutions for which filtration sterilization might not be possible. To determine if autoclave degrades peptide molecules, mass spectrometry (mass spec) analysis of peptides was performed before and after autoclave at 121° C. for 25 min at high pressure saturated steam. The results are shown in FIGS. 7-8 and FIGS. 9-10 for ST14 and T14, respectively, wherein the N-terminus and the C-terminus are not protected.

Figure 7:
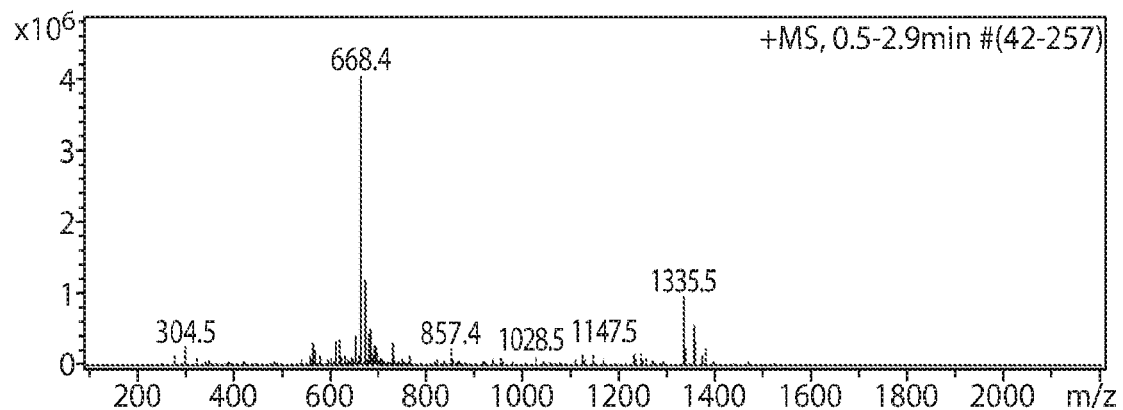
FIG. 7 is a graph of mass spectrometry of peptide ST14, in accordance with some embodiments.
Figure 8:
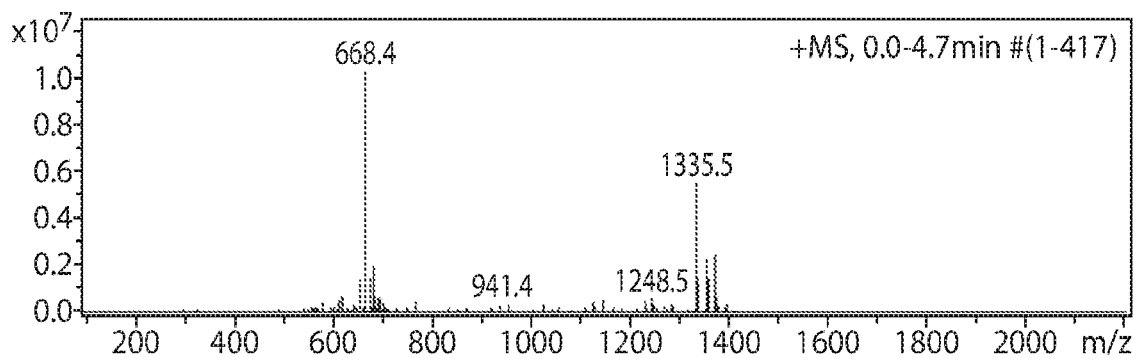
FIG. 8 is a graph of mass spectrometer of peptide ST14, in accordance with some embodiments.

The measured molar mass of ST14, prior to autoclave treatment, was 1335, which matches the calculated molar mass (FIGS. 7-8). ST14 did not degrade during autoclave treatment; therefore autoclave is an appropriate method for sterilization of ST14.

Figure 9:
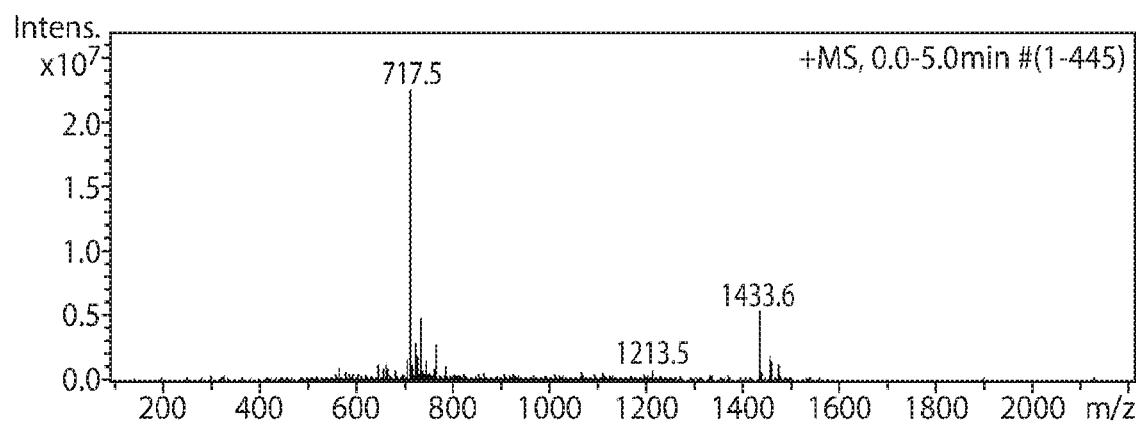
FIG. 9 is a graph of mass spectrometry of peptide T14, in accordance with some embodiments.
Figure 10:
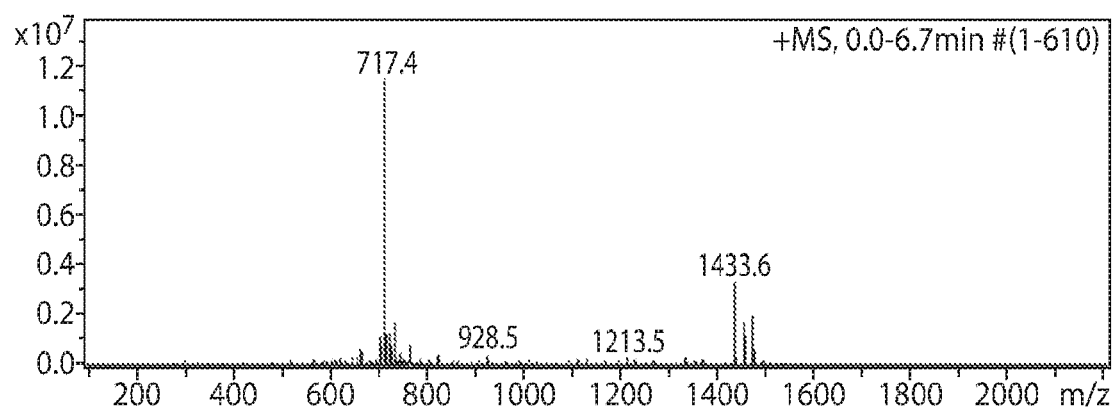
FIG. 10 is a graph of mass spectrometry of peptide T14, in accordance with some embodiments.

The measured molar mass of T14 is 1433, which matches the calculated molar mass. T14 did not degrade during autoclave, therefore autoclave treatment is an appropriate method for sterilization of T14, as shown in FIGS. 9-10.

Example 3: Peptide Solution Visual Appearance

ST14 and T14 were tested for dissolution in deionized water and appearance in solution at various concentrations. ST14 and T14 solutions were translucent at 1 percent, weight per volume (w/v) to 5 percent w/v. ST14 formed thick solutions at 1 percent, weight per volume (w/v) to 5 percent w/v, while T14 formed a thick solution at 5 percent w/v. This shows a difference between the two peptides that may indicate how they may behave under given conditions.

Example 4: pH of Peptide Solutions

The pH of the peptides in deionized water to provide a peptide solution were measured at various concentrations. The pH of the peptide solutions was measured at various concentrations. ST14 and T14 were tested. The recorded pH values ranged from about 1.9 to about 2.5. The results are listed in Table 2.

TABLE 2 pH values of ST14, and T14 at various concentrations.

| Peptide | Concentration | pH |
| --- | --- | --- |
| ST14 | 2.5% | 1.9 |
|  | 2.0% | 2.0 |
|  | 1.5% | 2.1 |
|  | 1.0% | 2.2 |
|  | 0.5% | 2.5 |
| T14 | 2.5% | 2.0 |
|  | 2.0% | 2.1 |
|  | 1.5% | 2.2 |
|  | 1.0% | 2.3 |
|  | 0.5% | 2.5 |

Example 5: Peptide Gel Formation

A Congo Red assay was performed to determine gel formation of peptide solutions in a PBS buffer solution (pH 7.4). 100 μl of each gel at varying concentrations were plated on a glass slide. After 30 seconds, 500 μl of a 1% Congo Red solution in PBS buffer (pH 7.4) was added around and on top of each of the gel aliquots and then the excess Congo Red solution was wiped off prior to examination.

Figure 11:
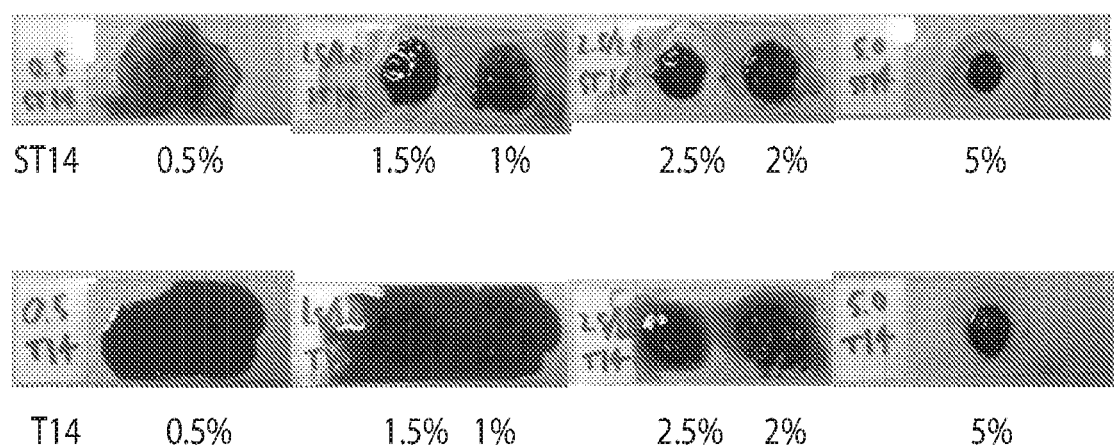
FIG. 11 are images related to gel formation with Congo Red buffer solution, in accordance with some embodiments.

ST14 and T14 were plated at varying concentrations of 0.5%, 1.0%, 1.5%, 2.0%, 2.5% and 5.0%. Visualization of gel formation determined the success or failure of gelation at each concentration. ST14 did not form a gel at 0.5%. T14 did not form a gel below 1%. The data are shown in FIG. 11.

Example 6: Effect of Concentration on the Rheological Properties

The rheological properties of the ST14 were evaluated at various concentrations using a rheometer (AR500, TA Instruments) with 40 mm plates. Peptide solution (700 μL) was placed on the rheometer plate and excess solution was gently removed by Kimwipes; measurements were performed after 2 minutes of relaxation time at 37° C. The storage modulus, loss modulus, and viscosity (η') were measured at 37° C. with the plates placed at a measuring geometry gap of 300 μm, and stress sweep tests were performed at 0.1 Pa~1000 Pa of oscillation stress with angular frequency at 10 rad/s.

Figure 12:
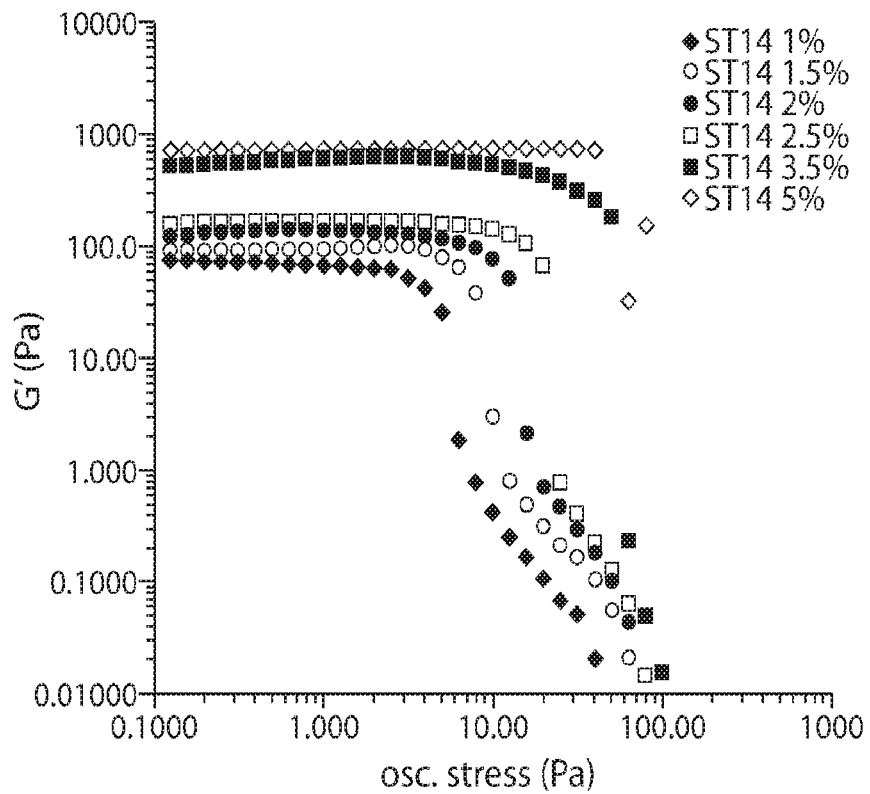
FIG. 12 is a graph plotting storage modulus versus oscillation stress of ST14, in accordance with some embodiments.
Figure 13:
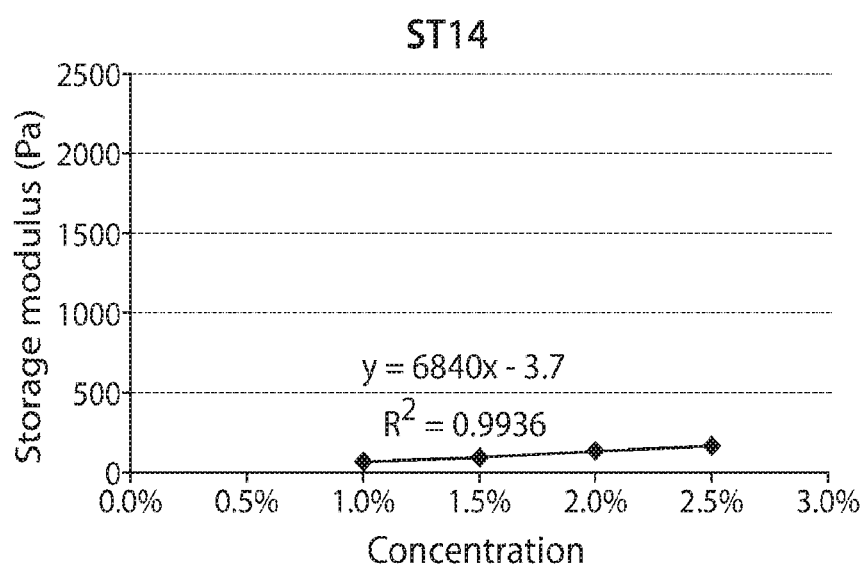
FIG. 13 is a graph plotting storage modulus versus concentration of ST14, in accordance with some embodiments.

The rheology results are shown in FIGS. 12 and 13 for ST14. The rheological properties of T14 were not measured. Rheological properties of ST14 at various concentrations is also shown in Table 3.

The storage modulus, yield stress, and max. viscosity of ST14 increased with increasing concentration. Based on its administration and use in anti-adhesion applications, the concentration of the peptide solution used may be adjusted to obtain the desired properties, for example storage modulus, loss modulus, yield stress and viscosity, for example, maximum viscosity.

TABLE 3

| | Rheological properties of ST14 | | | |
| --- | --- | --- | --- | --- |
| Concentration | Storage Modulus (G')* (Pa) | Loss Modulus (G')* (Pa) | Yield Stress (Pa)* | Max. Viscosity (max η') (Pa-s)* |
| 1 | 67 | 11.4 | 5.0 | 1.2 |
| 1.5 | 94 | 9.8 | 7.9 | 1.5 |
| 2 | 136 | 17.3 | 10.0 | 2.0 |
| 2.5 | 167 | 17.1 | 15.9 | 2.2 |

*At 1 Pa of oscillation stress

Example 7: Effect of Cell Culture Medium Contact on the Peptide Hydrogel Properties The effects of Dulbecco's modified Eagle's medium (DMEM) (pH 7.4) on the rheological properties of ST14 were evaluated on a rheometer (AR500, TA Instruments) with 40 mm plates. DMEM is a cell culture medium that contains 6.4 g/L of NaCl, 3.4 g/L NaHCO$_3$ (sodium bicarbonate), minor amounts of other salts, various amino acids, and 4.5 g/L of glucose. The pH of DMEM is 7.2±0.2 and the osmolality is 335±30 mOsm/Kg H$_2$O; both measurements are close to human physiological fluids such as blood. Peptide solutions (1%) were kept in 4° C. for at least 48 hours before testing. To perform the experiment, 1 mL of peptide solution was gently pipetted and placed on the plate of the rheometer. 2 mL of DMEM solution was gently added around the peptide solution. The peptide solution was treated with DMEM for two minutes, then the media was removed, and the plates were placed at a measuring geometry gap at around 450 μm. Measurements were performed at 37° C. after 2 min of relaxation time. Frequency tests were performed from 1 rad/s to 100 rad/s at 1 Pa of oscillation stress.

Figure 14:
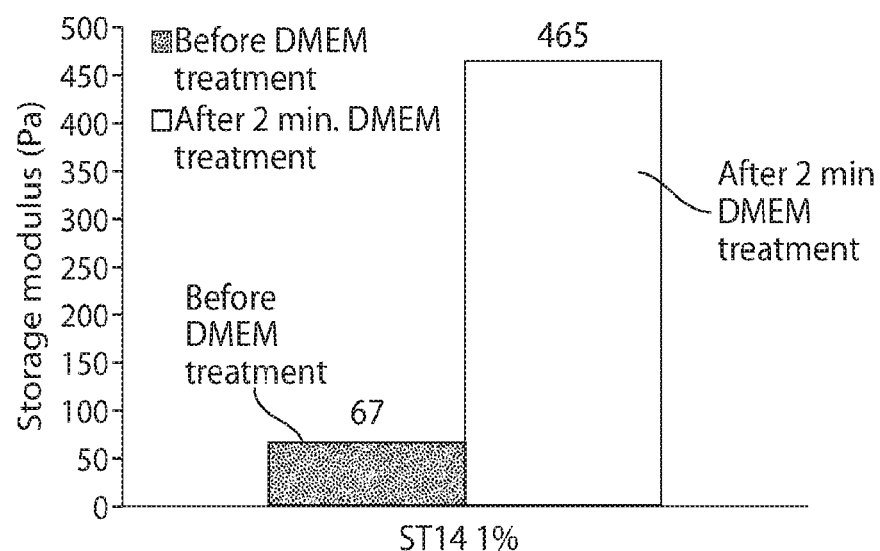
FIG. 14 is a graph plotting storage modulus of ST14 before and after DMEM treatment, in accordance with some embodiments.
Figure 15:
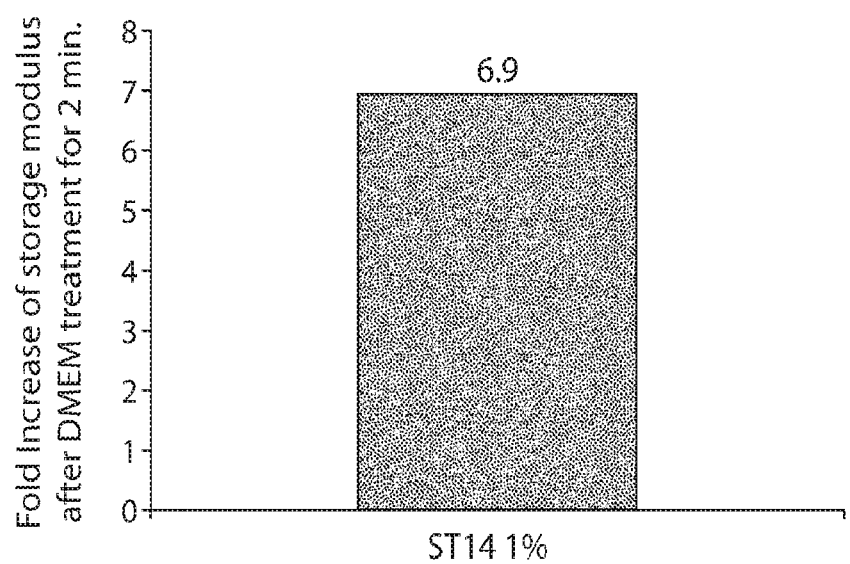
FIG. 15 is a graph plotting fold increase of storage modulus of ST14 after DMEM treatment, in accordance with some embodiments.

The rheological properties of ST14 (1%) were compared before and after DMEM treatment for 2 minutes in FIG. 14. Storage modulus data for untreated peptide solutions were taken from the data at 1 Pa and 10 rad/s in their stress sweep tests, and those for DMEM-treated peptide hydrogels were adapted from the data at 1 Pa and 10 rad/s in their frequency sweep test. The fold increase of storage moduli after DMEM treatment for 2 minutes is shown in FIG. 15. ST14 showed 6.9 fold increase of storage moduli after DMEM treatment.

This observation suggests that a critical intermolecular interaction arises after DMEM treatment, which determines the final stiffness after DMEM treatment. The change in pH and salt concentration may affect its rheological properties.

Example 8: Cell Viability Test

A cell viability (cytotoxicity) assay was performed to measure the ability of ST14 o support the viability of C57 BL/6 Mouse Mesenchymal Stem Cells (mMSCs)—a frequently-used cell line in hydrogel tissue culture systems. The hydrogel was prepared at a concentration of 2.5% and then diluted to concentrations of 1.5%, 1.25%, 1.0%, 0.75%, and 0.50% with sucrose, so that the final concentration of sucrose was 10%. Cells were washed and re-suspended in 10% sucrose to a final concentration of 5 million cells/ml. Cells were centrifuged and the supernatant was removed. The cells were re-suspended in each of the concentrations of hydrogels in 10% sucrose. The protocol was then followed for plating drop cultures and subsequent isolation as described in the PuraMatrix® Guidelines for Use (BD/ Corning website).

Figure 16:
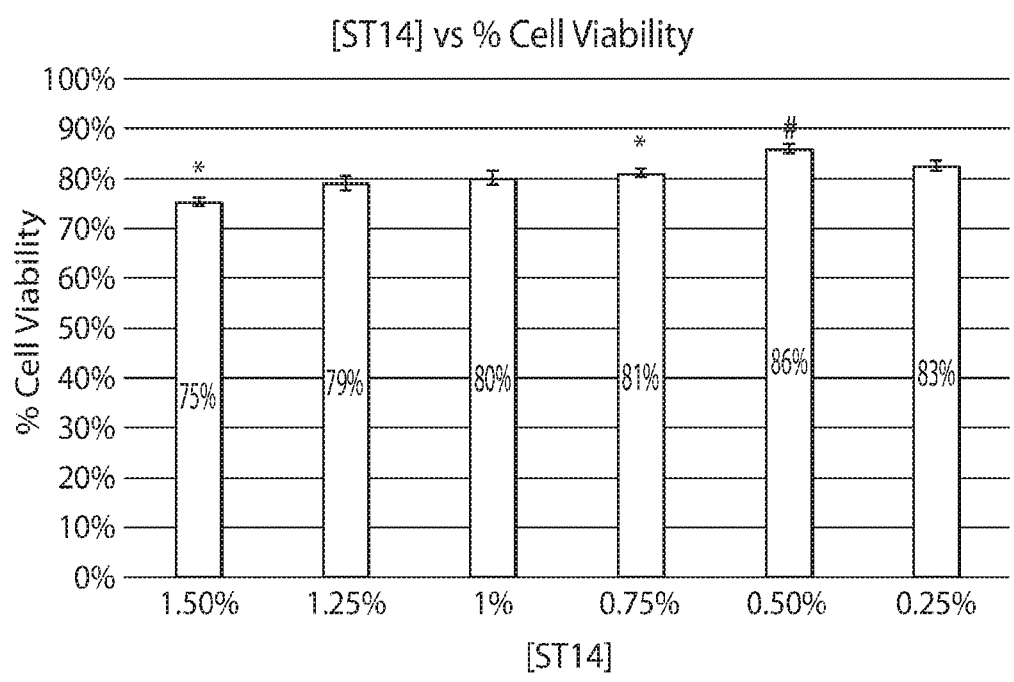
FIG. 16 is a graph plotting percent cell viability versus concentration of peptide, in accordance with some embodiments.

The results are shown in FIG. 16 for ST14. Cell viabilities significantly decreased when the concentration of peptides was over 0.75%.

In FIG. 16, "*" is noted when the cell viability is significantly lower than the cell viability at next lower concentration (p<0.05), and "#" is noted when the cell viability is significantly higher than the cell viability at next lower concentration (p<0.05).

Each of these Examples demonstrate the utility of self-assembling peptides in medical applications in which anti-adhesion or a prevention of adhesion is desired.

The invention claimed is:

1. A method of reducing adhesion in a subject, comprising:
   introducing a delivery device to the subject;
   positioning an end of the delivery device in a target area of the subject in which adhesion prevention is desired;
   administering through the delivery device a peptide solution comprising a self-assembling peptide, wherein the self-assembling peptide consists essentially of threonine or essentially of alternating amino acids of serine and threonine, wherein the self-assembling peptide comprises 14 amino acids, and wherein the administered peptide solution is in an effective amount and in an effective concentration to form a hydrogel scaffold under conditions at the target site to provide adhesion reduction;
   the effective amount comprises a volume from 1 mL to 5 mL;
   the effective concentration of the self-assembling peptide is between 1.0 weight per volume (w/v) percent to 5 weight per volume (w/v) percent; and
   removing the delivery device from the target site.

2. The method of claim 1, wherein the self-assembling peptide consists of alternating serine and threonine amino acids.

3. The method of claim 1, wherein the self-assembling peptide has the chemical structure (ST14):

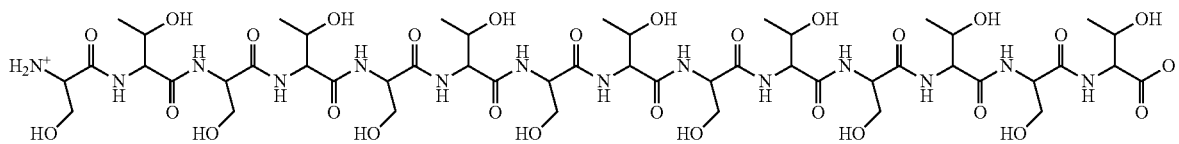 [SMILES: CC(O)C(NC(=O)C(CO)NC(=O)C(NC(=O)C(CO)NC(=O)C(NC(=O)C(CO)NC(=O)C(NC(=O)C(CO)NC(=O)C(NC(=O)C(CO)NC(=O)C(NC(=O)C(CO)NC(=O)C(NC(=O)C([NH3+])CO)C(C)O)C(C)O)C(C)O)C(C)O)C(C)O)C(C)O)C(=O)O]

4. The method of claim 1, wherein the self-assembling peptide consists essentially of consecutive threonine amino acids.

5. The method of claim 1, wherein the self-assembling peptide has the chemical structure (T14):

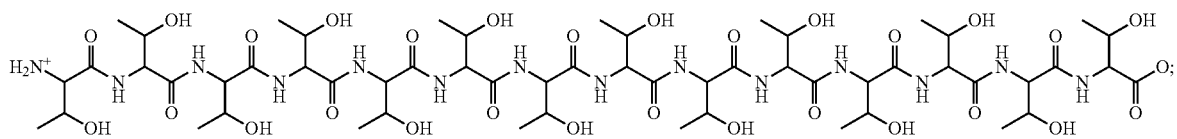

6. The method of claim 1, further comprising adjusting a pH of the peptide solution prior to administering the peptide solution.

7. The method of claim 3, wherein a storage modulus of the peptide solution increases between about 5 to about 10 times after exposure to physiological conditions.

8. The method of claim 1, further comprising visualizing the target site after a predetermined period of time to assess adhesion prevention.

9. The method of claim 1, wherein the method is used in one of an obstetric procedure and a gynecological procedure.

10. The method of claim 1, further comprising mixing the peptide solution with a cell solution prior to administration.

11. The method of claim 10, wherein the cell solution has a cell concentration of about 5 million cells per milliliter.

12. The method of claim 1, wherein the step of introducing is performed after a surgical procedure.

13. The method of claim 1, wherein the hydrogel scaffold comprises nanofibers having a diameter of less than about 5 nanometers.

* * * * *

UNITED STATES PATENT AND TRADEMARK OFFICE
CERTIFICATE OF CORRECTION

| | | |
|---|---|---|
| PATENT NO. | : 10,961,274 B2 | Page 1 of 1 |
| APPLICATION NO. | : 16/062801 | |
| DATED | : March 30, 2021 | |
| INVENTOR(S) | : Eun Seok Gil et al. | |

It is certified that error appears in the above-identified patent and that said Letters Patent is hereby corrected as shown below:

On the Title Page

In Item (72) delete the name "Marc Rioult" and add --Marika G. Rioult--.

Signed and Sealed this
Sixth Day of September, 2022

Katherine Kelly Vidal
*Director of the United States Patent and Trademark Office*